(12) United States Patent
Sakamoto et al.

(10) Patent No.: US 9,301,729 B2
(45) Date of Patent: Apr. 5, 2016

(54) ULTRASOUND DETECTING DEVICE HAVING FUNCTION OF CONFIRMING IRRADIATION POSITION, AND METHOD THEREOF

(75) Inventors: Naoko Sakamoto, Hino (JP); Jun Takeda, Hino (JP); Atsushi Asahina, Hino (JP)

(73) Assignee: Teijin Pharma Limited, Tokyo (JP)

( * ) Notice: Subject to any disclaimer, the term of this patent is extended or adjusted under 35 U.S.C. 154(b) by 0 days.

(21) Appl. No.: 13/388,797

(22) PCT Filed: Aug. 5, 2010

(86) PCT No.: PCT/JP2010/063675
§ 371 (c)(1),
(2), (4) Date: Feb. 3, 2012

(87) PCT Pub. No.: WO2011/016586
PCT Pub. Date: Feb. 10, 2011

(65) Prior Publication Data
US 2012/0130240 A1 May 24, 2012

(30) Foreign Application Priority Data
Aug. 5, 2009 (JP) .................. 2009-182485

(51) Int. Cl.
*A61B 8/00* (2006.01)
*A61B 8/08* (2006.01)
(Continued)

(52) U.S. Cl.
CPC ............. *A61B 8/0875* (2013.01); *A61B 8/5207* (2013.01); *A61N 7/00* (2013.01);
(Continued)

(58) Field of Classification Search
USPC ........................................ 600/438
See application file for complete search history.

(56) References Cited

U.S. PATENT DOCUMENTS 4,886,069 A * 12/1989 O'Donnell .................. 600/457
4,976,148 A * 12/1990 Migliori et al. ................. 73/579
(Continued)

FOREIGN PATENT DOCUMENTS

EP  0 064 399 A2  11/1982
EP  1 964 518 A1   9/2008
(Continued)

OTHER PUBLICATIONS

Extended European Search Report for Application No. 10806583.0-2319/2462873 PCT/JP2010063675 dated Jan. 7, 2013.
(Continued)

*Primary Examiner* — Tse Chen
*Assistant Examiner* — Lisa Kinnard
(74) *Attorney, Agent, or Firm* — Sughrue Mion, PLLC

(57) ABSTRACT

Provided is an ultrasound fracture detection device capable of accurately irradiating an ultrasound pulse to a target object, the device being characterized by being provided with an ultrasound wave irradiating transducer, a signal receiving transducer which receives a reflected wave of an ultrasound wave irradiated from the ultrasound wave irradiating transducer, a signal, storage unit which stores a received signal, and a display unit which displays an analysis program that analyzes a stored signal, a determination program that performs determination from the result of the analysis and/or performs determination from the stored signal, and the result of the analysis and/or the result of the determination, wherein the determination program performs the determination using that information relating to the received signal varies depending on the reflector within a living organism.

12 Claims, 8 Drawing Sheets
(5 of 8 Drawing Sheet(s) Filed in Color)

(51) Int. Cl.
*A61N 7/00* (2006.01)
*A61B 17/17* (2006.01)

(52) U.S. Cl.
CPC .... *A61B 17/1703* (2013.01); *A61N 2007/0013* (2013.01); *A61N 2007/0052* (2013.01); *A61N 2007/0073* (2013.01)

(56) References Cited

U.S. PATENT DOCUMENTS

| | | | | |
|---|---|---|---|---|
| 5,241,515 | A | * | 8/1993 | Harms et al. ............... 367/105 |
| 5,653,237 | A | * | 8/1997 | Uchida ....................... 600/456 |
| 6,964,640 | B2 | * | 11/2005 | Zumeris et al. ............. 600/459 |
| 7,300,403 | B2 | * | 11/2007 | Angelsen et al. ............ 600/447 |
| 7,588,539 | B2 | * | 9/2009 | Petersen ..................... 600/459 |
| 2005/0070795 | A1 | | 3/2005 | Karasawa |
| 2005/0171429 | A1 | * | 8/2005 | Mathew et al. ............. 600/437 |
| 2007/0032733 | A1 | * | 2/2007 | Burton ........................ 600/509 |
| 2008/0018199 | A1 | * | 1/2008 | Trolier-McKinstry et al. ............................ 310/311 |
| 2008/0089178 | A1 | * | 4/2008 | Knittel ......................... 367/98 |
| 2010/0168574 | A1 | | 7/2010 | Takabayashi et al. |

FOREIGN PATENT DOCUMENTS

| | | | |
|---|---|---|---|
| EP | 1964518 A1 | * | 9/2008 |
| JP | 2005-125081 A | | 5/2005 |
| JP | 2009-183454 A | | 8/2009 |
| WO | WO 2007/069775 A1 | | 6/2007 |
| WO | WO 2008/018612 A1 | | 2/2008 |

OTHER PUBLICATIONS

International Search Report of PCT/JP2010/063675 dated Nov. 16, 2010.

* cited by examiner

ULTRASOUND DETECTING DEVICE HAVING FUNCTION OF CONFIRMING IRRADIATION POSITION, AND METHOD THEREOF

CROSS REFERENCE TO RELATED APPLICATIONS

This application is a National Stage of International Application No. PCT/JP2010/063675 filed Aug. 5, 2010, claiming priority based on Japanese Patent Application No. 2009-182485 filed Aug. 5, 2009, the contents of all of which are incorporated herein by reference in their entirety.

TECHNICAL FIELD

The present invention relates to an ultrasound detecting device having function of confirming irradiation position and a method therefor, and particularly to a method or a device for detecting a target or confirming appropriate irradiation using ultrasound waves.

BACKGROUND ART

When an ultrasound therapy is applied as an orthopedic treatment, an irradiation position of the ultrasound waves needs to be determined so that the ultrasound waves are appropriately irradiated to an affected area. As a method therefor, an X-ray photograph of the affected area is sometimes used, but since the X-ray photographs are two-dimensional information, determination of a correct irradiation position or angle to a target in a part with a thick tissue such as an upper arm region or a femoral region is difficult.

As a prior-art technology, as described in Patent Document 1, a device which determines that ultrasound waves are irradiated at a fracture part is known, but this is a device for determination using that the ultrasound waves are propagated in the long-axis direction of a bone and is different from the present invention. Also, Patent Document 2 discloses a method of irradiating ultrasound waves to a bone and of using the reflective waves thereof.

In the ultrasound therapy, in order to reliably obtain treatment efficiency, the determination of an appropriate position or angle of ultrasound irradiation is an indispensable technology in an ultrasound irradiation device for treatment.

CITATION LIST

Patent Document

Patent Document 1: International Publication No. 2008/018612
Patent Document 2: International Publication No. 2007-069775

SUMMARY OF THE INVENTION

Problems to be Solved by the Invention

An object of the present invention is to provide a device which enables accurate irradiation of ultrasound waves and a method therefor. Also, another object of the present invention is to make accurate determination of an irradiation position or an irradiation angle to a target possible, in the case where the target in a living body is not easily found from the outside or in the case of a part with a thick soft tissue such as an upper arm region or a femoral region, for example.

Means for Solving Problems

The present invention solves the problems by the following means.

That is, the present invention is configured as follows:

(1) An ultrasound detecting device which detects an ultrasound irradiation position by irradiating an ultrasound pulse to a living body, provided with:

one or a plurality of ultrasound wave irradiation transducers which transmit ultrasound waves and one or a plurality of signal receiving transducers which receive reflective waves of the ultrasound waves irradiated from the ultrasound wave irradiation transducers;

a signal storage unit which stores a received signal received by the signal receiving transducers;

an analysis program for analyzing a stored signal stored by the signal storage unit;

a determination program for determining whether or not an obtained reflective wave is obtained from a target of ultrasound wave irradiation by using an analysis result by the analysis program and/or the stored signal; and a display unit which displays one or more selected from a group consisting of the stored signal, the analysis result, and the determination result by the determination program, characterized in that the analysis program and/or the determination program makes analysis and/or determination by using that information of the received signal is different depending on the difference of a reflector within the living body.

(2) The ultrasound detecting device described in (1), characterized in that the analysis program and/or the determination program makes analysis and/or determination by using a frequency and/or voltage parameter of the received signal.

(3) The ultrasound detecting device described in (1) or (2), characterized in that the analysis program makes analysis by using a difference in intensity distribution of a frequency component of the reflective wave caused by a difference in a reflector within the living body.

(4) The ultrasound detecting device described in (2) or (3), characterized in that the analysis program calculates a ratio of a high-frequency component to a low-frequency component of the frequency in the received signal of the obtained reflective wave.

(5) The ultrasound detecting device described in (4), characterized in that the high-frequency component and the low-frequency component of the frequency to be used in the analysis program is selected from two types of bands, that is, a central frequency of a transmission ultrasound wave and the band in the vicinity thereof and a second peak frequency and the band in the vicinity thereof (6) The ultrasound detecting device described in (4), characterized in that the high-frequency component and the low-frequency component to be used in the analysis program are maximum values in a band of 1.5±0.1 MHz and a band of 1.2±0.1 MHz.

(7) The ultrasound detecting device described in any one of (1) to (6), characterized in that the determination program makes determination by comparison between the analysis result in the analysis program and a numerical value set in advance.

(8) The ultrasound detecting device described in any one of (1) to (7), characterized in that the determination program makes determination by comparison between the highest voltage in the reflective wave and a numerical value set in advance.

(9) The ultrasound detecting device described in any one of (1) to (8), characterized in that when a plurality of reflective waves are obtained at successively different irradiation angles at one installed position of the ultrasound wave irradiation transducer/or at successively different positions on the body surface, the display unit displays time information, voltage and/or a ratio of the high-frequency component to the low-frequency component in the frequency included in each of the plurality of reflective waves in color cells of the corresponding time and angles in accordance with numerical values on a map indicating the time information on the vertical axis and the angle on the lateral axis.

(10) The ultrasound detecting device described in (9), characterized in that, when the numerical value exceeds the numerical value set in advance, there are a plurality of angles detected to be highly likely to be the target and they are set to a target angle range, an angle optimal for treatment is at the center of the target angle range.

(11) The ultrasound detecting device described in any one of (1) to (10), characterized in that a range of time for analyzing the received signal and/or a range of time for storing the received signal and/or a range of time for determination by the determination program is determined by a time range setting program set in advance in the analysis program.

(12) The ultrasound detecting device described in (11), characterized in that the time range setting program takes an envelope line of a voltage of a reflection signal, and with regard to a waveform of the envelope line having a value of a voltage A or more at the top, a point at which the voltage returns to a value C when inclination of an envelope line at a voltage B is positive is set to be a detection start time, wherein a relationship of A≥B>C holds for A, B, and C, and a certain time interval starting at the detection start time is set as an analysis target range.

(13) The ultrasound detecting device described in (11), characterized in that the time range setting program takes, in a limb section, a ratio of a distance from a point on a limb periphery to a bone directly below to the limb periphery (distance/periphery) for a plurality of individuals, a coefficient is set to ((average value of the ratios of the plural individual data)±(k×standard deviation)), and when a limb periphery of a subject is obtained, a twofold number of a distance range determined by a method for predicting the distance range from the point on the periphery to the bone directly below by multiplying the limb periphery of the subject by the coefficient is divided by a sound speed in the soft tissue so as to determine the time interval, which is set to an analysis target range.

(14) The ultrasound detecting device described in any one of (1) to (13), characterized in that the ultrasound wave irradiation transducer also works as the signal receiving transducer.

(15) The ultrasound detecting device described in any one of (1) to (14), characterized in that the ultrasound detecting device detects a bone as a target.

(16) The ultrasound detecting device described in any one of (1) to (15), characterized in that the ultrasound detecting device detects a tumor/or a degenerated tissue within the body as the target.

(17) The ultrasound detecting device described in any one of (1) to (16), characterized in that the ultrasound detecting device is integrated with an ultrasound treatment instrument.

(18) The ultrasound detecting device described in any one of (1) to (17), characterized in that a cured state of the target is determined on the basis of temporal change of the stored signal, the analysis result or the determination result by the determination program at the same irradiation position.

Each of the above-described configurations can be combined with each other unless it does not depart from the gist of the present invention.

Advantages of the Invention

By using the ultrasound detecting method or device of the present invention, accurate irradiation of the ultrasound waves to the target is made possible. Also, if the position of the target cannot be easily found from the outside or in the case of a part with a thick soft tissue such as a femoral region or an upper arm region, for example, appropriate irradiation of the ultrasound waves and determination of an irradiation angle to the target can be realized.

BRIEF DESCRIPTION OF THE DRAWINGS

The patent or application file contains at least one drawing executed in color. Copies of this patent or patent application publication with color drawings will be provided by the Office request and payment of the necessary fee.

BEST MODE FOR CARRYING OUT THE INVENTION

The inventors paid attention to the characteristics that, when ultrasound waves advance in a medium, they are reflected on a boundary surface having different acoustic impedance and the ultrasound characteristics of the reflective waves are different due to a difference in the acoustic impedance on the boundary surface and damping characteristics of the medium, and achieved determination of an appropriate irradiation position and direction of an ultrasound beam to a target by determining that the reflective waves of the ultrasound waves are generated from the target of the irradiation. Also, in the present invention, by receiving the reflective waves by using a transmitting transducer, it is possible to realize detection by a single transducer. Moreover, the ultrasound detecting method or a device of the present invention can detect the reflective waves by using one or more parameters among a voltage, a frequency, and signal occurrence time in the reflective waves and by using a threshold value determined by those empirical values and the like.

[Application Example]

The present invention will be described on the basis of an embodiment illustrated in the attached drawings. In this embodiment, the target will be described as a bone, but the ultrasound detecting device of the present invention can be also used for any bone in the body such as limbs, a trunk, and a head of a human or animal, internal organs, degenerated tissues such as a tumor and the like. That is, the device can be used only if the target has a boundary surface having different acoustic impedance inside, and the ultrasound characteristics of the reflective waves are different due to the difference in the acoustic impedance on the boundary surface or damping characteristics of the medium. Thus, the present invention is not limited to the illustrated embodiment.

Figure 1:
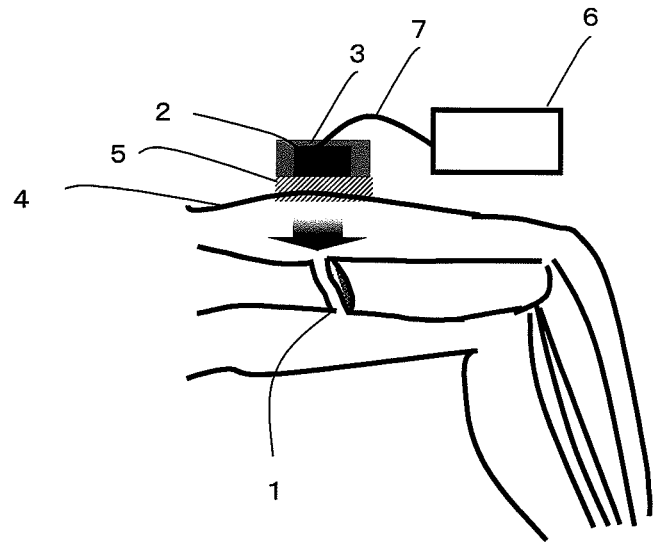
FIG. 1 is a schematic diagram illustrating an irradiation example to a femoral fracture treatment.

An application example of the present invention to a femoral fracture treatment is illustrated in FIG. 1. FIG. 1 is an example of a bone or a fracture position in which the target is in femora having a thick soft tissue. If a fracture part 1 is to be treated, a transmission/reception transducer 2, which is an ultrasound wave irradiation transducer and signal reception transducer, is installed at an attaching position determined in a medical institution and attached to the femora using a fixing device 3. The fixing device 3 can be anything as long as it can load the transmission/reception transducer 2 and fix it to a body surface 4, and a cylindrical device having a belt or the like, for example, is used. In this case, an ultrasound propagation substance 5 is interposed between the transmission/reception transducer 2 and the body surface 4. The ultrasound propagation substance 5 may be anything as long as it propagates ultrasound waves and water, ultrasound gel and the like, for example, are suitable.

The ultrasound detecting device or method of the present invention is used when appropriate irradiation position and/or direction to an affected area (a target of the ultrasound wave irradiation) is determined at an examination or during an ultrasound treatment for outpatients or in a medical institution such as a ward and before and after or during the ultrasound treatment at a patient's home. The affected area might be a bone or a fractured part if an ultrasound fracture treatment device (SAFHS (registered trademark), for example) is used. For detection on whether or not the ultrasound waves have been irradiated to the target, reflective ultrasound waves received by the transducer is used, and it does not matter whether the detecting device or the method thereof of the present invention is integrated with or separate from the ultrasound fracture treatment device or the like. As an example of a use mode, the transducer is installed at a position at which a doctor or the like determines ultrasound wave irradiation by an X-ray image (in the case of a femora region, only the long-axis direction is determined by a doctor), the ultrasound waves are irradiated, and on the basis of the reflective waves from the body received by the transducer, it is detected whether or not appropriate irradiation is made to the target. Accurate ultrasound wave irradiation is realized by switching the transmitted waves of the transducer to the ultrasound waves for treatment or by replacing the transducer by a treatment transducer depending on the detected position and/or angle.

[Device Configuration]

In the ultrasound detecting device or method of the present invention, the same transducer can be used for transmission/reception since the reflective waves of the ultrasound waves are used. Also, the ultrasound wave irradiation transducer and the signal receiving transducer may be constituted by separate transducers so that the reflective waves of the ultrasound waves transmitted by one or a plurality of transducers are received by another one or a plurality of transducers. For example, there may be various modes such that the ultrasound waves are transmitted by one transducer and the reflective waves are received by installing a plurality of transducers at all the positions that can be predicted to be reached by the reflective waves or at all the positions where the presence of the reflective waves, and distribution of parameters such as voltage, intensity distribution of a frequency component are to be known, or that the reflective waves are received by installing a plurality of transducers at all the positions that can be considered to be able to irradiate ultrasound waves to the target and by installing a plurality of transducers at the positions that can be predicted to be reached by the reflective waves or at all the positions where the presence of the reflective waves, and distribution of parameters such as voltage, intensity distribution of a frequency component are to be known.

Also, by using the same transducer for the transmission/reception transducer and the transducer to be used for treatment, switching of transducers after a bone is detected or a fracture is detected becomes unnecessary, and treatment can be made at an accurate position and direction. Moreover, by integrating the ultrasound detecting device of the present invention with the treatment instrument, the irradiation position can be detected regardless of timing such as before, during or after the treatment, and even if the irradiation position is changed due to an influence of an attitude in the middle of the treatment, irradiation can be made correctly to the bone or the fracture part, which is a target.

Figure 2:
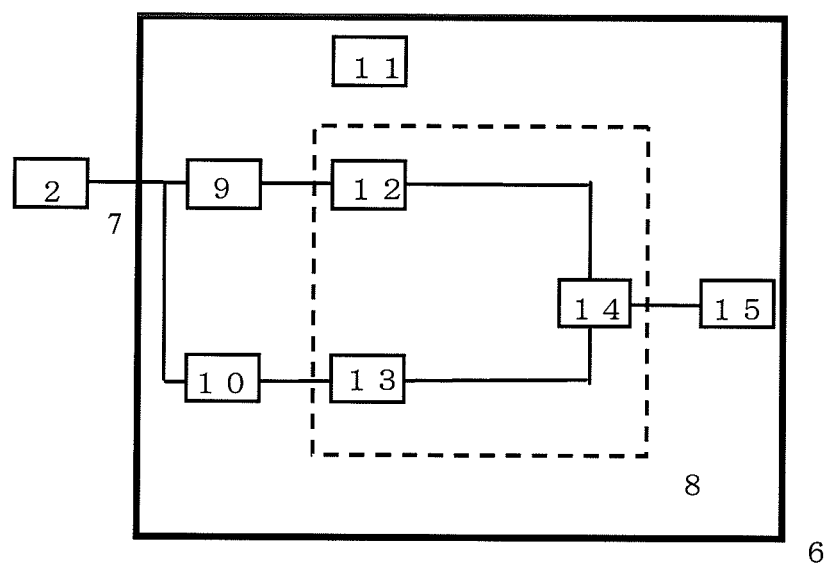
FIG. 2 is a schematic diagram illustrating device constituent elements in the present invention.

FIG. 2 illustrates device constituent elements in the present invention. A determining device 6 is provided with a transmission circuit 9, a reception circuit 10, a control unit 8 including a transmission condition setting unit 12, a signal storage unit 13, and a determination program 14, power supply means 11, and a display unit 15. An operation in the actual device will be described below.

First, the control unit 8 supplied with power from the power supply means 11 sends a driving signal to the transmission circuit 9 under a transmission condition set by the transmission condition setting unit 12. The transmission circuit 9 that received the driving signal sends a signal to the transmission/reception transducer 2 via a cable 7, and the transmission/reception transducer 2 transmits ultrasound waves. In this case, the receiving side sends a trigger signal to the reception circuit 10 at a timing when the control unit 8 sends the driving signal to the transmission circuit 9 or the transmission is stopped and starts signal detection. Here, the power supply means 11 such as a built-in power supply, an external power supply or the like specifically supplies power to each part of the determining device 6.

The ultrasound waves received from the transmission/reception transducer 2 are converted to an electric signal and sent to the reception circuit 10 via the cable 7. The detected signal is stored by the signal storage unit 13 or analyzed by an analysis program for analyzing the stored signal and determined by using the determination program 14 on the basis of the determination condition set in advance. The result is displayed by the display unit 15, and determination on whether the waves are irradiated to the bone or not can be made. Here, the signal storage unit 13 can be specifically a semiconductor memory and the like. Also, the display unit 15 can be specifically an LCD which displays the result in characters, numerical values, signal waveforms, graphs or images or LED which displays the result by lighting or the like.

If the ultrasound detecting device or method of the present invention is integrated with the treatment device, by determining an appropriate irradiation position before the treatment, the treatment can be started immediately by switching the wave from the ultrasound waves for bone detection to the treatment ultrasound waves. If the determining device 6 can also transmit the treatment ultrasound waves, the both conditions are switched for use as necessary by the transmission circuit 9. If the determining device 6 cannot transmit the treatment ultrasound waves, only the determining device of the main body ultrasound detecting device or the entire main body having the determining device and the transducer is changed to a treatment instrument, and the treatment is started.

[Transmission/Reception Condition of Ultrasound Waves]

As the irradiation condition of detection ultrasound waves, ultrasound waves with an appropriate condition for the target are used.

As the transmission conditions of the appropriate detection ultrasound waves in the case of bone detection or fracture detection, for example, a frequency of 1.5 MHz, a burst width of 5 µs, repetition frequency of 10 Hz, time average and space average of ultrasound output of 0.042 mW/cm$^2$ are preferable, and as reception conditions, a sampling frequency of 20 MHz, amplification of 20 dB, LPF of 10 MHz, and HPF of 100 kHz are preferable. Regardless of the above-described conditions, it is only necessary that the burst width, for example, is shorter than the time from transmission of the ultrasound waves to reception by the transducer after reflection from the bone or the fracture part, and if the distance from the transducer to the bone is 40 mm, assuming that the sound speed in the soft tissue is 1585 mm/sec, it should be at least shorter than 50.5 µs ((distance L)×2/(sound speed V)=40 (mm)×2/1585 (m/sec)=50.5 (µsec)). Also, it is only necessary that the repetition frequency, the ultrasound output, and the amplification are within a range of safe conditions for a living body and the reflective waves from the bone or the fracture part as a target can be obtained even if damping of the ultrasound waves in the medium is considered.

For the treatment ultrasound waves, ultrasound waves with appropriate conditions for fracture treatment are used. As the appropriate ultrasound wave conditions, for example, ultrasound waves with a frequency of 1.5 MHz, a burst width of 200 µs, a repetition frequency of 1 kHz, and time average and space average of the ultrasound output of 30 mW/cm$^2$ are preferable.

[Acquisition of Parameters Required for Determination]

Figure 3:
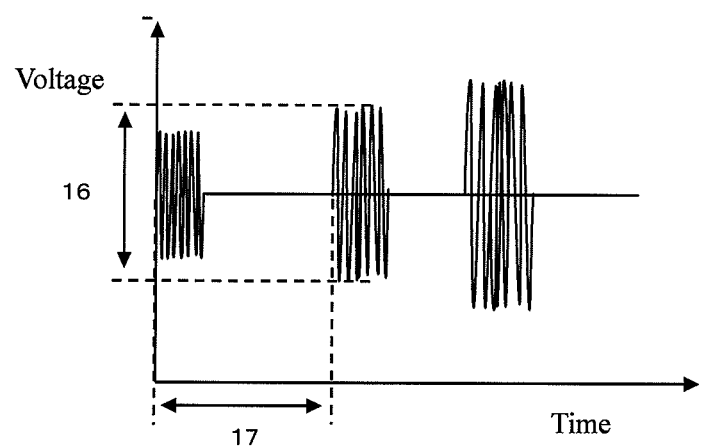
FIG. 3 is a schematic diagram in which a reflective wave is converted and obtained as a detection signal.
Figure 4:
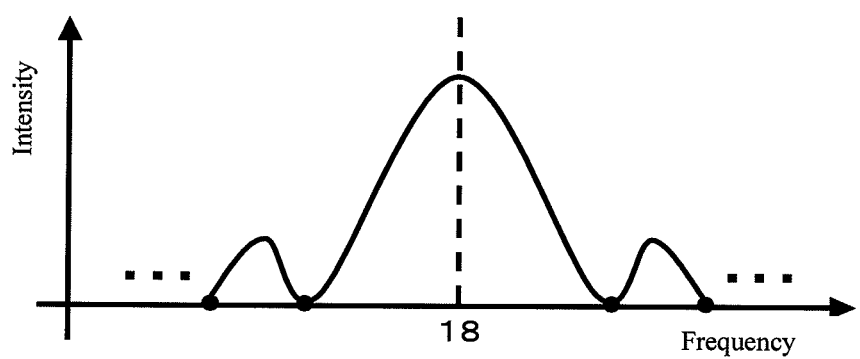
FIG. 4 is a schematic diagram illustrating an example of intensity distribution of a frequency component.

A reflection signal obtained under the above-described transmission/reception conditions is converted by the transducer 2 to a format or information suitable for determination. An example of the detection signal after conversion is illustrated in FIG. 3. An example of intensity distribution of a frequency component after the conversion is illustrated in FIG. 4.

First, the reflective waves are converted by the transducer 2 from a sound pressure to an electric signal and transmitted to the determining device 6, and the amplitude of the reflective waves is obtained as a voltage 16 and a distance twice (reciprocal movement) that from the transducer to a reflector (where reflective waves of the transmission ultrasound waves are generated) is obtained as time 17. The frequency component is obtained by applying analysis processing to the reflective waves in FIG. 3. Methods of observing the frequency component included in the waveform include FFT analysis, and by applying FFT analysis in a range including the reflective waves to be analyzed, the intensity distribution of the frequency component included in the range can be obtained. FIG. 4 is a diagram illustrating intensity distribution of the frequency component obtained around a central frequency 18 of the transmission waves as a model. From the above process, the voltage (amplitude), the time (distance), and the frequency component can be obtained as information of the reflective waves. The signal storage unit of the present invention stores raw data of the waveform, that is, signal intensity to the time information in all the data and the like, and the analysis program obtains frequency information by analyzing the received signal.

[Determination]

With respect to of the voltage (amplitude), the time (distance), and the intensity distribution of the obtained reflective waves, a value calculated from the values of the acoustic impedance, the damping coefficient, and the sound speed cited from various documents and/or the value obtained from the basic experiments is set as a threshold value of the numerical values set in advance, and determination is made on whether the reflector is obtained from the target by comparing them. For example, the numerical values are cited in "Ultrasound Wave Handbook" published by Maruzen Co., Ltd, "Basic Knowledge and Safety Management of ME" supervised by the Japan Society of Medical Electronics and Biological Engineering, published by Nankodo, "Medical Ultrasound Equipment Handbook" by Corona Publishing Co., Ltd. An example of determination using the threshold value determined by the basic experiments will be described below.

First, in general, the voltage of the reflection signal is determined under the influences of damping until the signal reaches the reflector, the reflective surface shape of the reflector, the acoustic impedance on the reflective boundary surface, and damping until the signal reaches the detector. Assuming the application to the ultrasound fracture treatment method, the voltage is subject to the influences of the damping in the soft tissue until the signal reaches the bone, the bone shape, the acoustic impedances in the soft tissue and the bone, and the damping in the soft tissue until the signal reaches the transducer.

Figure 5:
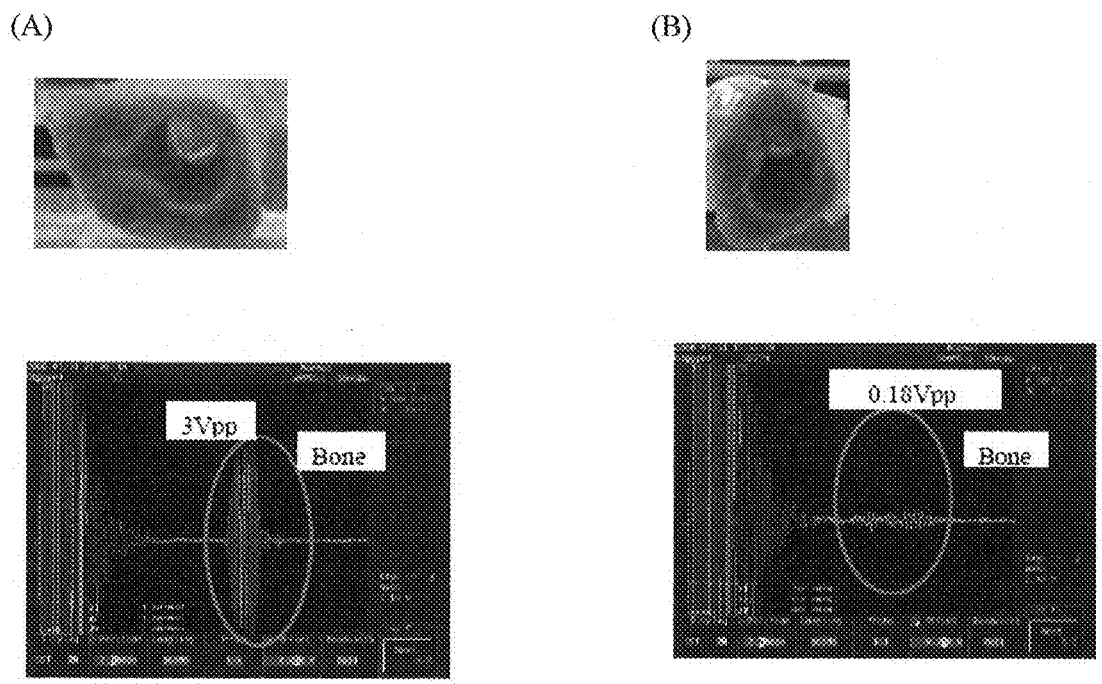
FIG. 5 is a result of basic experiments for confirming that a reflective wave of a pig bone is largely changed depending on the shape.

When the ultrasound waves propagate through the medium, reflection occurs on the boundary surface having different acoustic impedance. In a living body, since the acoustic impedance is different not only in the soft tissue and the bone but also in various tissues in the soft tissue such as fascia, blood capillaries, muscle fibers and the like, reflection occurs from various boundary surfaces in the process of propagation. Particularly, since the difference in the acoustic impedance between the bone and the soft tissue is extremely larger than the difference between heterogeneous soft tissues, if there is no influence of the reflective surface shape, damping or the like, the bone generates reflective waves larger than those between heterogeneous soft tissues. However, it was confirmed in the basic experiments that the reflective waves generated on the bone reflective surface having a large radius of curvature (FIG. 5B) have amplitude smaller than the reflective waves generated on the bone reflective surface having a small radius of curvature (FIG. 5A), and the amplitudes of the reflective waves are largely different depending on the difference in the radius of curvature. In a living body, the influence of damping and the like are also added to that of the reflective surface shape of the bone, there are some cases in which the reflective waves obtained from the bone might become smaller than the reflective waves obtained from those between the heterogeneous soft tissues. In principle, the bone has a cylindrical structure and the surface has a convex shape with a radius of curvature larger than that of the soft tissue, and thus, the reflective waves are scattered. Also, among the reflective waves generated in the soft tissue those generated at a position closer to the body surface than at the bone have a shorter distance through which the ultrasound waves are transmitted, and thus, the influence of the damping caused by transmission through the soft tissue is smaller. As described above, if the positional relationship among the transducer, the soft tissue, and the bone in the irradiation of the ultrasound waves is disadvantageous to bone reflection, the soft-tissue reflective waves become larger than the bone reflective waves. Therefore, since determination only on the basis of the voltage is difficult under these conditions, it is preferable to set up conditions combining time and/or a frequency in addition to the voltage and also to use them in the determination by the determination program. Since the voltage can be used for determination without applying special processing to the received reflective waves, it has a merit that the software configuration can be simplified. If the voltage is used for determination, the voltage information of the received signal stored in the signal storage unit can be used as it is and compared with the value set in advance in the determination program (which becomes a threshold value).

Figure 6:
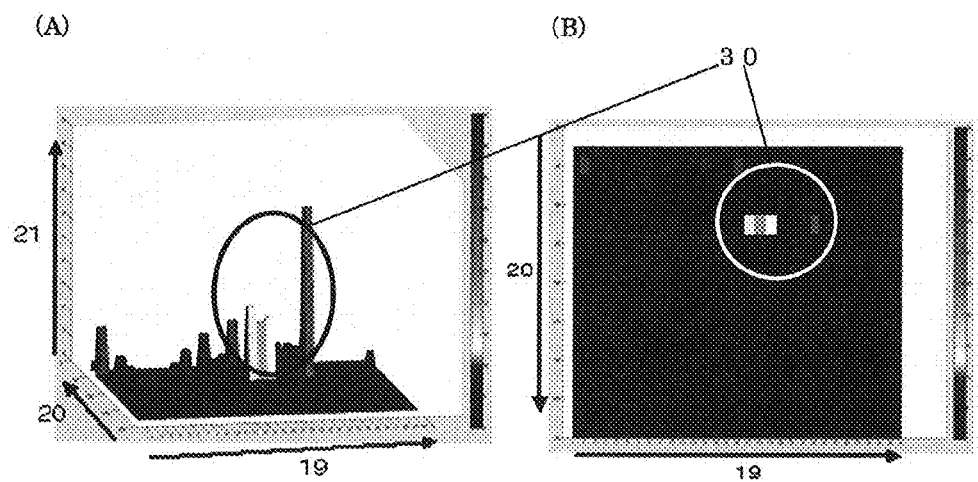
FIG. 6 is a result display example displayed as three-dimensional information by plotting a data number on the X axis, time on the Y axis, and a voltage on the Z axis.

The time refers to time from transmission to reception of the ultrasound waves, and since the product of the sound speed and time makes a distance, the values of the sound speeds listed in the literature can be used to calculate a propagation distance to the reflection target. That is, since the half of the total propagation distance represents a distance from the body surface to the reflector, by comparing the distance with the distance from the body surface to the bone predicted on the basis of anatomical knowledge in the case where the bone is a target, for example, it is possible to determine whether the obtained reflective waves originate at the depth substantially equal to the depth of the bone or not. For example, it can be realized by attaching metal (visible in an X-ray image) to the body surface of the femora, photographing the X-ray image from the lateral direction of the femora and predicting the distance between the metal and the bone. However, since there is a soft tissue which can become a reflector also at the depth substantially equal to the depth of the bone, determination not only on the basis of the time information but also on the basis of combination of a voltage, a frequency and the like is preferable. For example, by installing a transducer at a certain position on the femoral surface, a plurality of reflective waves are continuously obtained by changing only the angle of the transducer in the short-axis direction of the bone without changing the position, and displayed as three-dimensional information by plotting a data number (19) on the X axis, time (20) on the Y axis, and a voltage (21) on the Z axis. Subsequently, the reflector is estimated from prediction obtained from the anatomical knowledge obtained in advance and the visual information having continuity (FIG. 6A) and the like. FIG. 6B illustrates an example in which the Z axis displaying the voltage (21) is eliminated from the three-dimensional display in FIG. 6A and the data number (19) is plotted on the X axis and the time (20) is plotted on the Y axis so as to make two-dimensional display. In both FIG. 6A and FIG. 6B, a spot (30) detected to exceed the pre-set threshold value and to be likely a bone is displayed by using colors like red or yellow that enables discrimination from the other spots.

Figure 7:
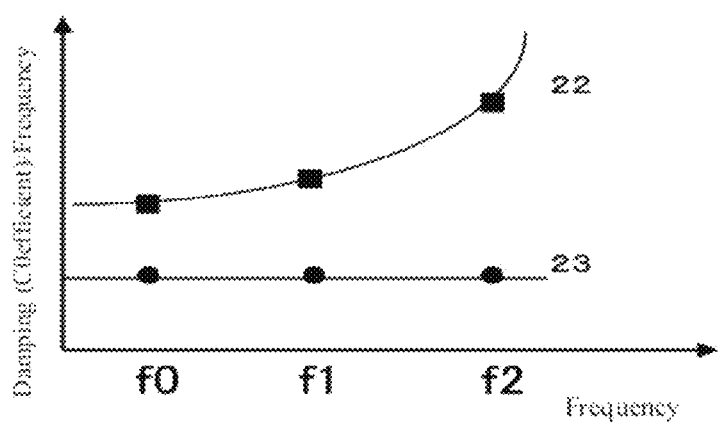
FIG. 7 is a schematic diagram of damping characteristics of propagation ultrasound waves in a bone and a soft tissue.

With regard to the frequency, a difference in the damping characteristics of the propagation ultrasound waves in the bone and the soft tissue is used. A schematic diagram of the damping characteristics of the propagating ultrasound waves in the bone and the soft tissue is shown in FIG. 7. The damping characteristics of a living tissue is different depending on the tissue, and a bone (22) is known to have a characteristic that the high-frequency component included in the propagating ultrasound waves attenuates more than in a soft tissue (23).

Figure 8:
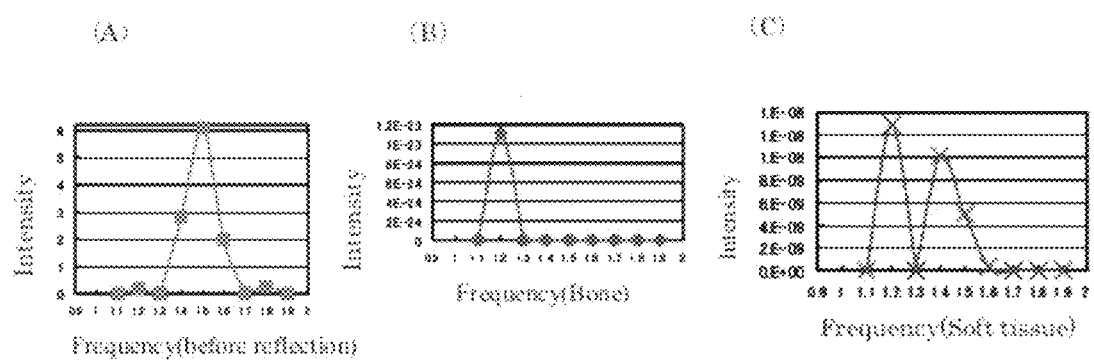
FIG. 8 is an example illustrating a change in the intensity distribution of the frequency component by theoretical calculation.

With regard to this difference in the characteristics, occurrence of difference in the intensity distribution of the frequency components included in the reflective waves has been confirmed by theoretical calculations and basic experiments. FIG. 8 shows the results of the basic experiments. FIG. 8A shows the intensity distribution in each frequency component immediately after the irradiation of the ultrasound waves at 1.5 MHz. After the application of ultrasound wave, each frequency component in the reflection from the bone is shown in FIG. 8B, and each frequency component in the case of reflection from the soft tissue is shown in FIG. 8C. From the above, it is found that FIG. 8B shows damping in the high-frequency component that is larger than that of FIG. 8C, by taking into consideration the ratio of the frequencies close to 1.2 MHz with respect to the frequency close to 1.5 MHz. Therefore, by paying attention to the intensity distribution of the components included in the reflective waves in the frequency, determination can be made whether the reflection comes from the bone or from the soft tissue.

A range of FFT analysis for finding a frequency component is determined by a range setting method determined in advance. Then, in the specified range, analysis on whether the waves are bone reflective waves or soft tissue reflective waves is made under the analysis conditions set in advance for waveform recognition such as a voltage value. The analysis method for finding a frequency component is not limited to FFT but may be a method that can find the frequency component.

Figure 9:
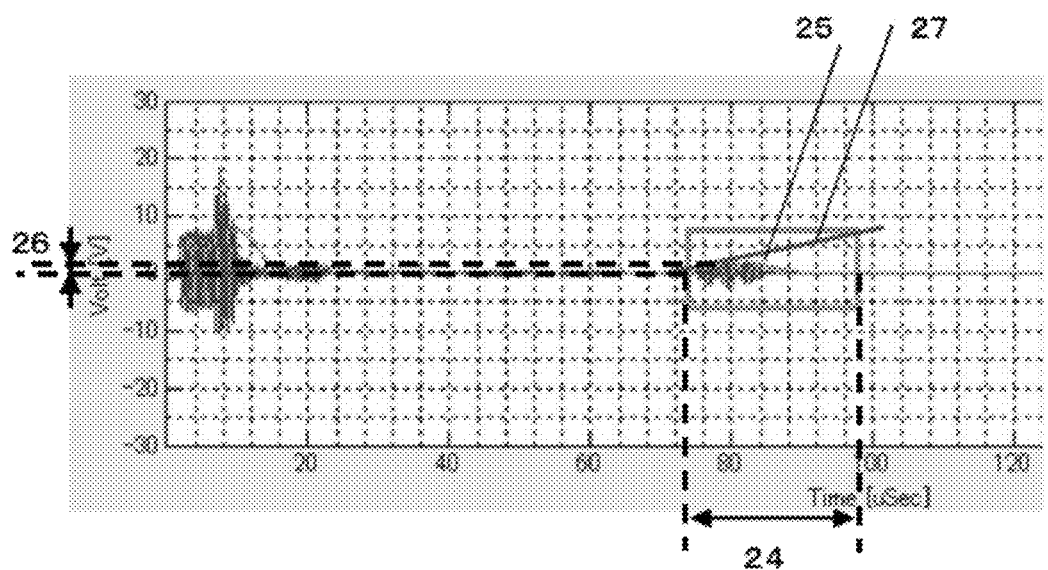
FIG. 9 is a specific example of signal detection.

A specific example of signal detection/FFT analysis is shown in FIG. 9. With respect to the obtained reflection signal, an analysis target range is defined as a duration having some margin including a signal part or a duration starting from the time when the reflective waves are first returned (assuming that the time at which the ultrasound waves are irradiated is set to 0, approximately a time obtained by adding to 0 the time required for the ultrasound waves to travel the doubled distance from the body surface that is measured or obtained from the literature to the bone which is a target) and including the reflective waves from the bone surface on the side opposite to the bone surface of the target to which the ultrasound waves are irradiated.

As a specific example, if the ultrasound waves having a burst width of 5 μsec are transmitted, duration 24 of 30 μsec starting at rising of the signal part is set as an analysis target range or the like. As a specific example of a method of determining the detection start point of the signal, such a method can be cited that an envelope line 25 of the reflection signal in the analysis target range is taken, and regarding the waveform having a value exceeding the voltage A (0.4 V (26) in FIG. 9) that is larger than a noise voltage as a top, if inclination (27) of the envelope line at the voltage B (0.4 V in FIG. 9) is positive, the point at which the voltage is returned to the voltage C (0.1 V in FIG. 9) along the envelope line is set as the detection starting time. Under these conditions, the relationship of $A \geq B > C$ holds for the voltages A, B, and C. The voltage C is assumed to be a voltage larger than the noise voltage but smaller than the voltage A, and the voltage B is a voltage determined by the relationship of $A \geq B > C$. The bone has a cylindrical shape, and reflection occurs on the outer surface, the lumen surface and the like, and thus, a plurality of reflective waves might return with shifted timing. It is only necessary that the duration for analysis is longer than the duration including the reflective waves returned from the bone outer surface and the lumen surface to which the ultrasound waves are irradiated among the plurality of reflective waves that are returned from the bone with shifted timing.

As an analysis method, attention is paid to the difference in the damping characteristics in the bone reflective waves and the soft tissue reflective waves, and an analysis set in advance is applied to the measured values and the numerical value obtained as a result is compared with the pre-set value.

A specific analysis method is that, for example, a ratio of the amounts among two or more kinds of frequency component included in the measured results is calculated. For example, they are the two types, that is, a central frequency and the band in the vicinity thereof of the transmission ultrasound waves and a second peak frequency lower than the central frequency and the band in the vicinity thereof. In this case, with respect to the maximum value in the central frequency and the band in the vicinity thereof in the transmission ultrasound waves and the maximum value in the second peak frequency lower than the central frequency and the band in the vicinity thereof, a higher frequency is referred to as a high-frequency component and a lower frequency is referred to as a low-frequency component.

Figure 10:
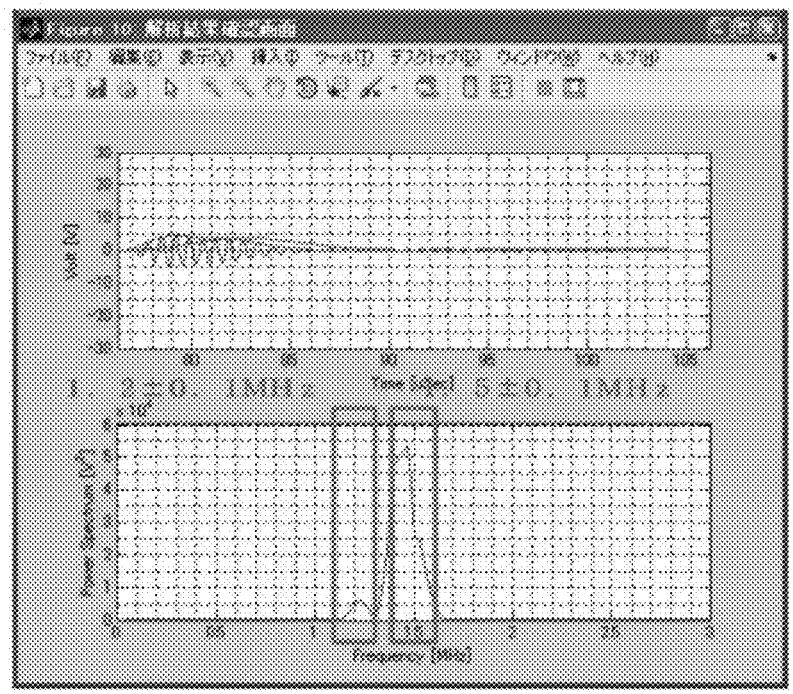
FIG. 10 is a specific example of FFT analysis.

Specific calculation example is as follows. If the central frequency of the transmission ultrasound waves is 1.5 MHz and the second peak is present at 1.2 MHz, the maximum value in the band of 1.5±0.1 MHz in the frequency distribution of the reflective waves is compared with the maximum value in the band of 1.2±0.1 MHz, and the maximum value of the band of 1.2±0.1 MHz is divided by the maximum value of the band of 1.5±0.1 MHz. The lower figure in FIG. 10 illustrates a frequency component of the reflective waves obtained when the ultrasound waves having the central frequency at 1.5 MHz and the second peak at 1.2 MHz are transmitted, and the ratio of the amount of frequency component in this case is 0.6/5.3=0.11.

Regarding the values calculated in this analysis, the larger the damping in the high frequency is, the larger value is shown in the calculated frequency component ratio. Thus, since the high-frequency component in the propagating ultrasound waves undergoes damping more in the bone than in the soft tissue, the value of the analysis result is larger in the bone reflective waves than in the soft tissue reflective waves. The low-frequency component is divided by the high-frequency component in the above, but the ratio may be found by dividing the high-frequency component by the low-frequency component.

The analysis is applied to the measured value and compared with the pre-set value (which becomes the threshold value) so as to make bone determination by the determination program.

Figure 11:
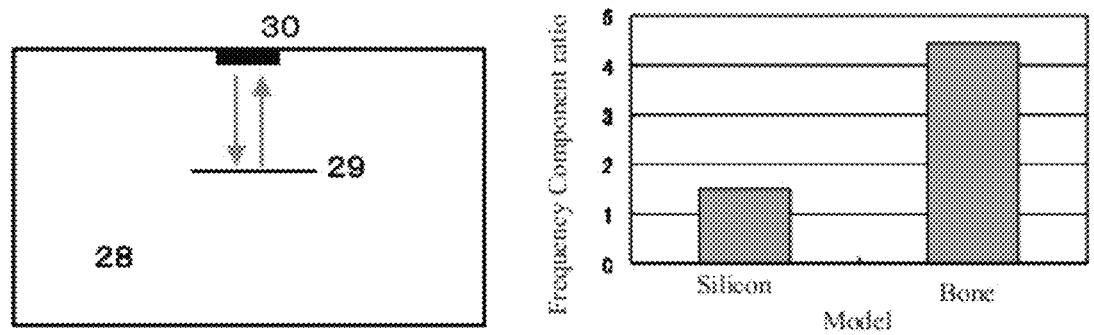
FIG. 11 is a specific example of frequency component calculation in the basic experiments using a model.

The pre-set value is set by using the result obtained by the basic experiments. It is known from the basic experiments that, with respect to the reflective waves from the bone and the reflective waves from the soft tissue, the values calculated by the above analysis method are different (the numerical value is larger in the bone), and the threshold value is set so that only the reflective waves from the bone can be detected. As a specific example, the results of the basic experiment using a model are shown in FIG. 11. A reflector model 29 is set in water 28, and a pig bone is used as a bone model and silicone rubber as a soft tissue model. For the reflective waves obtained, the frequency component ratios calculated by the above-described analysis method indicate that the ratio for the bone model is 4.5 with respect to that for the soft tissue model 1.5, resulting in a factor 3 difference. In this case, by setting the threshold value to 2, for example, determination of the bone can be made such that if the component ratio is larger than 2, it indicates a bone.

The frequency component ratio is obtained by applying special processing such as the FFT analysis and calculation of a component ratio to the received reflective waves as described above, and the algorithm or the device configuration in the processing becomes more complicated than the case in which other reflective wave information is used, but since the frequency component ratio can be used for the determination regardless of the size of the voltage value, it can be used even if the voltage value cannot be sufficiently obtained.

Thus, the bone determination can be made by using the frequency component ratio also in a part having a thick soft tissue or a part having a large radius of curvature of the bone shape on the reflective surface where a sufficient voltage cannot be obtained. Also, by creating an algorithm for making determination by combining time and voltage with the frequency component ratio, determination accuracy is further improved.

The ultrasound detecting device of the present invention uses that the reflective waves from the bone is different from the reflective waves from the part other than the bone in the above-described reflective wave information such as the voltage, the frequency component and the like, and can make bone detection, fracture position detection or soft tissue detection by using one or more pieces of information.

Determination of bone/fracture or soft tissue is performed by any one or more of the methods of determination using a threshold value set in advance; determination by directly displaying information and adding judgment by a user such as a doctor (selection of the maximum value of amplitude, for example); and determination by displaying plural pieces of data through mapping and adding judgment of a user such as a doctor or the like.

If the threshold value is used, bone or fracture position is determined by the device. For example, the threshold value is set on the basis of the reflective wave data of the bone and the soft tissue actually measured in advance under the transmission/reception conditions in the development stage. As an example of the threshold value, the bone is supposed to be irradiated if the voltage value is 4 Vpp or more under the conditions where the voltage of the reflective waves obtained from the soft tissue is less than 4 Vpp, or if the value of frequency component ratio is 10 or more under the conditions where the frequency component ratio of the reflective waves obtained from the soft tissue is less than 10, or if the time is 40 μs or more under the conditions where it can be judged that the reflective waves from the bone cannot exist in a time less than 40 μs due to the positional relationship between the bone and the transducer, for example. If the threshold value is exceeded, the result is displayed to the user by lighting of a lamp or the like and the user is notified that the irradiation under the transducer installation conditions (position and angle) is appropriate.

If the information is displayed directly, the information relating to the reflective waves and the like are displayed on the determining device or a numerical display unit provided separately, and a user such as a doctor determines appropriate irradiation on the basis of the information. The numerals on the display unit changes with the change in the installed position or direction on the body surface of the transducer, for example, and the user adds anatomical and ultrasound physical knowledge and determines by him/herself the boundary between the bone tissue and the soft tissue such that a position and/or a direction indicating the maximum value or the value of 90% or more thereof is appropriate. Other than the numerical display, there can be expression by display by a scale, brightness of a lamp, speed of lamp flashing, presence of sound, tone of the sound, intervals of pulse sound and the like, and they may be combined with each other. The user such as a doctor determines the appropriate irradiation position and/or irradiation angle by combining the above-described information with clinical information.

Figure 12:
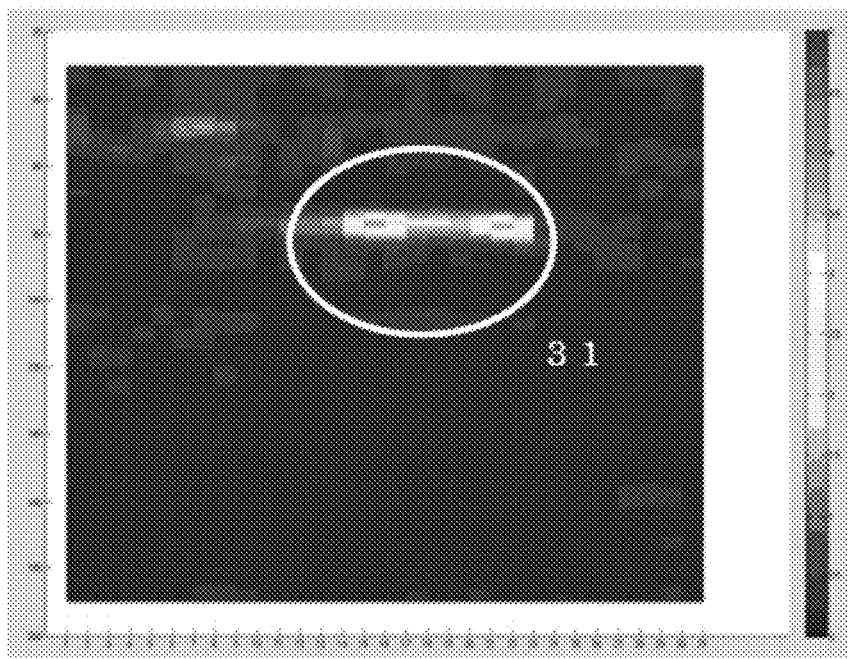
FIG. 12 is a specific example of imaging of a voltage by mapping.
Figure 15:
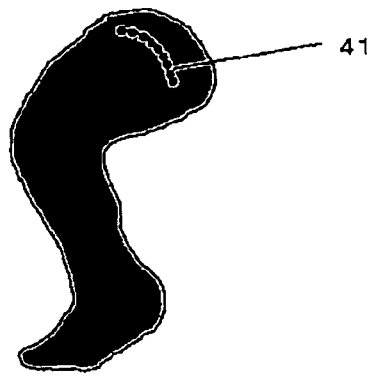
FIG. 15 is a specific example illustrating continuous different positions on the body surface on the femora.

If the values are to be mapped and imaged, the user such as a doctor makes determination on the basis of image information indicating presence or features of the bone tissue and the soft tissue, which are displayed targets. For example, regarding a plurality of pieces of data obtained by successively different irradiation angles at one position, if time information and a measured value (voltage and/or frequency) are obtained, respectively, for data of one angle, the time information is mapped on the vertical axis and the irradiation angle is mapped on the lateral axis and then, the measured values are color-coded in accordance with the cells of time and irradiation angles in accordance with the numerical value. As a color coding method, visual identification is sufficient, and classification such that the voltage less than 2 Vpp is indicated in blue and the voltage at 4 Vpp or more in red, for example, can give also visual information to the users. In this case, the voltage at 4 Vpp or more indicates that it is likely to be the reflective waves from the bone, while the voltage less than 2 Vpp indicates that it is likely to be the reflective waves from the soft tissue. A map in which the measured value is a voltage is shown in FIG. 12 as an example. By setting an image pattern in advance and by comparing the value with it, the device determines the bone or the fracture position or a user such as a doctor makes determination by combining knowledge. In this case, a bright region in FIG. 120 (31) is in red color and indicates that it is highly likely to be a bone. The plurality of pieces of data displayed on the map do not have to be limited to the plurality of pieces of data obtained at successively different irradiation angles at one position but may be a plurality of pieces of data obtained at successively different positions on the body surface. The successively different positions on the body surface are positions 41 successively arranged with intervals of 1 to 20 mm in a linear manner on the femora in FIG. 15, for example.

Figure 13:
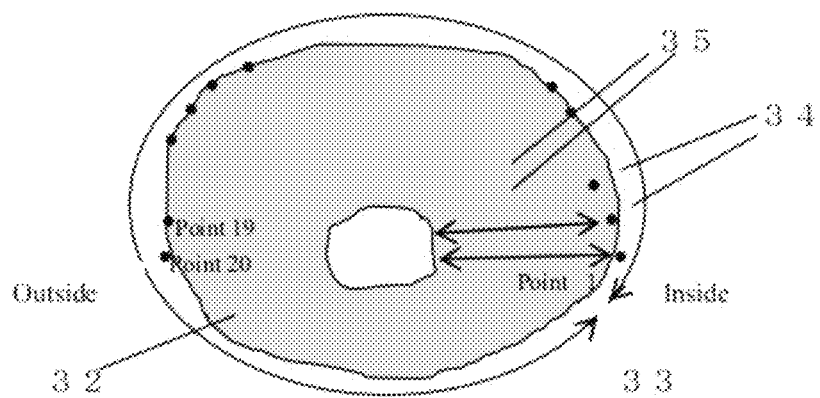
FIG. 13 is a schematic diagram illustrating a specific example of a method of predicting a distance between the body surface and the bone.

If the time information is set in advance, it is obtained by using a predicted value of the bone depth obtained by using an existing ultrasound imaging device or an X-ray device, a prediction coefficient of bone depth calculated from the relationship between the femoral periphery and the internal structure or obtained from a coefficient indicating a relationship between the internal structure of the front side of the femoral region and the internal structure of the entire femoral region, for example. A specific example regarding the prediction coefficient of bone depth calculated from the relationship between the femoral periphery and the internal structure is shown below by using FIG. 13. In a specific femoral section 32 on the femora set in advance, a plurality of femoral peripheral diameters (33) of a subject are obtained, and at points (34) which equally divide the peripheral upper side (body front side) into 20 parts (the point 1 side is the inside, and the point 20 side is on the outside), an ultrasound diagnostic image is obtained, and a distance between the body surface and the bone surface (35) in the whole image is measured. The periphery of the specific femoral section corresponds to the position of the femora which can be a measurement target or the periphery of a center part in the long-axis direction in the femora, for example, but this is not limiting. The (distance/femoral periphery) at each of the 20 points of all the subjects is calculated and an average ($\mu$) and standard deviation ($\sigma$) are obtained. From the obtained average ($\mu$) and standard deviation ($\sigma$), the prediction section ($\mu \pm k\ \sigma$) of the population is calculated. Reference character k is a numeral to be multiplied by the standard deviation ($\sigma$) so as to adjust the size of the range of a prediction section. For example, it may be k=1.96, which expresses a 95% confidence interval in statistics. This is used as a coefficient for setting time information set in advance, and if the periphery at the same femoral long-axis position of the patient is known, the coefficient is multiplied by this prediction section and the range of the bone depth is predicted to be a depth (cm) having some range. A quotient obtained by dividing this range by the sound speed is calculated, and occurrence time of the reflective waves is predicted. The occurrence time is predicted from the femoral periphery because the femoral periphery and the bone depth are different depending on the patient. In the above, the part is equally divided into 20 parts, but the division may be made in accordance with the required number of the irradiation positions, and if the irradiation position is known, equal division is not necessary but it is only necessary to obtain the data at the irradiation position.

Figure 14:
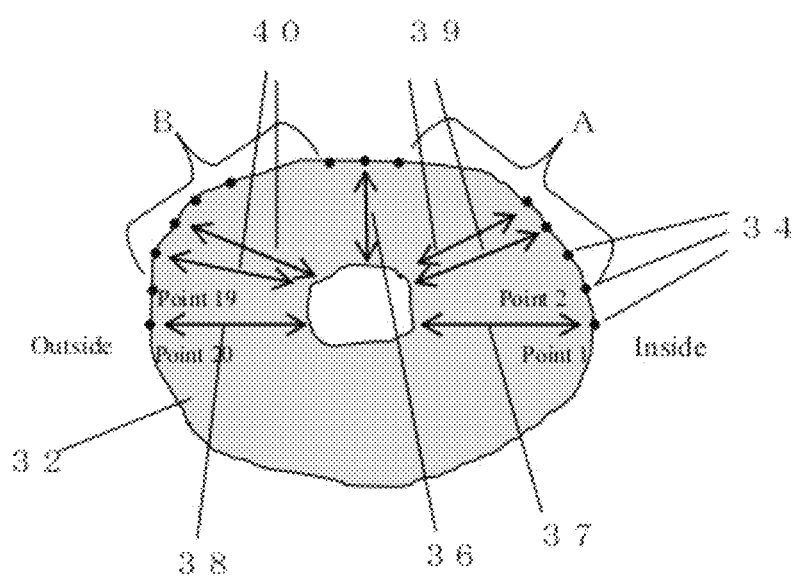
FIG. 14 is a schematic diagram illustrating another specific example of a method of predicting a distance between the body surface and the bone.

Also, another specific example will be described on the basis of FIG. 14. In a femoral section (32), at points 34 from 1 to 20 which equally divide the half of the front side (the point 1 side is on the body inside and the point 20 side is on the body outside), distances from the body surface at 11, 1, and 20 to the bone are calculated in advance (they are a(36), b(37), and c(38), respectively). The points from the point 2 to the point 10 are collectively referred to as points A, and a distance d(39) from the body surface to the bone at the points A is calculated by "d=a×((b/a−1)×(11−A)/(11−1)+1)", and the points from the point 12 to the point 19 are collectively referred to as points B, and a distance e(40) from the body surface to the bone at the points B is calculated by "e=a×((c/a−1)×(B−11)/(20−11)+1)", and the twofold number of d at the points A and the twofold number of e at the points B are divided by the sound speed in the soft tissue so as to calculate the distance between the body surface and the bone, and the occurrence time of the reflective waves is predicted. If a point is at a reference numeral n, the distance from the body surface to the bone at the specific point is calculated according to the above equation, and the occurrence time of the reflective waves can be predicted.

Also, instead of predicting the range of the bone by the above-described method, the depth of the soft tissue present at the depth closer to the body surface than the bone may be predicted by measuring the depth of the soft tissue, and the region further than the range is set as a prediction range of the bone depth.

In all the described determination methods, the threshold value or the range of the value may be changed or adjusted by taking into account of a phenomenon of a gradual change in the reflective wave information from the fracture part, a target, associated with curing or a difference due to individual difference.

It is also possible to know the process of curing from the displayed numerical values and to know treatment effects in addition to appropriate treatment. The fracture part exhibits a slightly swollen shape in the curing process, subsequently is completely cured and the swelling is resolved, and is brought into a state in which gentle continuity with the bone tissues in the vicinity is formed. The voltage of the reflection signal is strongly affected by the shape as described above, and the voltage is predicted to gradually increase as the shape changes from a bulge to a substantially flat state. Also, in the fracture part, a blood tumor is generated in the affected area and a cross-bridge is formed by a granulation tissue, and calcium is deposited on a chondroid tissue that has replaced the area, resulting in a normal bone tissue in the curing process. That is, since the affected area is replaced from a tissue in a state close to a soft tissue to a bone tissue, and thus, a change with curing is predicted to occur also in the frequency. Specifically, the frequency component ratio is predicted to gradually increase with curing. Thus, the present invention can also determine the cured state of the target on the basis of a temporal change of the stored signal, analysis result or determination result by the determination program at the same irradiation position. The determination in this case may be performed by a doctor or the like, or determining means may be provided which sets a cure threshold value and makes the display unit display completion of the cure when the cure threshold value is reached.

The present invention may be used for search of a degenerated tissue such as a tumor in a bone tissue or a soft tissue and the like other than for determination of different tissues such as a bone and a soft tissue.

INDUSTRIAL APPLICABILITY

By using the ultrasound detecting method or device of the present invention, the ultrasound waves can be accurately irradiated to a target even in any bone in the body such as limbs, a trunk, and a head of a human or animal, internal organs, degenerated tissues such as a tumor and the like.

REFERENCE SIGNS LIST 1 fracture part
2 transmission/reception transducer
3 fixing device
4 body surface
5 ultrasound propagation substance
6 determining device
7 cable
8 control unit
9 transmission unit
10 reception unit
11 power supply means
12 transmission condition setting unit
13 signal storage unit
14 determination program
15 display unit
16 voltage
17 time
18 frequency
19 data number
20 time
21 voltage
22 bone data
23 soft tissue data
24 duration
25 envelope line of reflection signal
26 voltage
27 inclination of envelope line at 0.4 V
28 in water
29 reflector model
30 transmission/reception transducer
31 region which is likely to be a bone
32 femoral section
33 femoral peripheral diameter
34 point
35 distance between body surface and bone surface
36 a
37 b
38 c
39 d
40 e
41 successively different positions on body surface

The invention claimed is:

1. An ultrasound detecting device which detects an ultrasound irradiation position by irradiating an ultrasound pulse to a living body, comprising:
one or a plurality of ultrasound wave irradiation transducers which transmit ultrasound waves and one or a plurality of signal receiving transducers which receive reflective waves of the ultrasound waves irradiated from said ultrasound wave applying transducers;
signal storage which stores a received signal received by said signal receiving transducers;
an analysis program for analyzing a stored signal stored by said signal storage;
a determination program for determining whether or not an obtained reflective wave is obtained from a target of ultrasound wave irradiation by using an analysis result by said analysis program or the stored signal; and
a display which displays one or more selected from a group consisting of said stored signal, said analysis result, and said determination result by said determination program,
wherein
said analysis program calculates a ratio between a high-frequency component and a low-frequency component of the frequency in the received signal of the obtained reflective wave, and
said analysis program or said determination program makes analysis or determination by using the fact that a frequency or voltage parameter of the received signal is different depending on a difference of a reflector within the living body,
wherein said analysis program makes analysis by using a difference in intensity distribution of a frequency component of the reflective wave caused by a bone characteristic that the high-frequency component included in the propagating ultrasound waves attenuates more than in a soft tissue,
wherein in said analysis program, at least one range of time selected from the group consisting of a range of time for analyzing the received signal, a range of time for storing the received signal and a range of time for determination by the determination program is determined by a time range setting program set in advance,
wherein said time range setting program takes an envelope line of a voltage of a reflection signal, and with regard to a waveform of the envelope line having a value of a voltage A or more at the top, a point at which the voltage returns to a voltage C when inclination of an envelope line at a voltage B is positive is set to be a detection start time, a relationship of $A \geq B > C$ holds for A, B, and C, and a certain time interval starting at the detection start time is set as an analysis target range, and
wherein said time range setting program takes, in a limb section, a ratio of a distance from a point on a limb periphery to a bone directly below to the limb periphery (distance/periphery), for a plurality of individuals a coefficient is set to ((average value of said ratio of the plural individual data) ± (k × standard deviation)), and when a limb periphery of a subject is obtained, a twofold number of a distance range determined by a method for predicting the distance range from the point on the periphery to the bone directly below by multiplying said limb periphery of the subject by said coefficient is divided by a sound speed in the soft tissue so as to determine the time interval, which is set to an analysis target range.

2. The ultrasound detecting device according to claim 1, wherein
the high-frequency component and the low-frequency component of the frequency to be used in said analysis program is selected from two types of bands, that is, a central frequency of a transmission ultrasound wave and the band in the vicinity thereof and a second peak frequency and the band in the vicinity thereof.

3. The ultrasound detecting device according to claim 1, wherein
the high-frequency component and the low-frequency component to be used in said analysis program are maximum values in a band of 1.5±0.1 MHz and a band of 1.2±0.1 MHz.

4. The ultrasound detecting device according to claim 1, wherein
said determination program makes determination by comparison between the analysis result in said analysis program and a numerical value set in advance.

5. The ultrasound detecting device according to claim 1, wherein
said determination program makes determination by comparison between the highest voltage in the reflective wave and a numerical value set in advance.

6. The ultrasound detecting device according to claim 1, wherein
when a plurality of reflective waves are obtained at successively different irradiation angles at one installed position of the ultrasound wave irradiation transducer or at successively different positions on the body surface, said display displays time information, voltage or a ratio between the high-frequency component and the low-frequency component in the frequency included in each of the plurality of reflective waves in color cells of the corresponding time and angles in accordance with numerical values on a map indicating the time information on the vertical axis and the angle on the lateral axis.

7. The ultrasound detecting device according to claim 6, wherein
if said numerical value exceeds said numerical value set in advance, there are a plurality of angles detected to be highly likely to be the target, and they are set to a target angle range, an angle optimal for treatment is at the center of said target angle range.

8. The ultrasound detecting device according to claim 1, wherein
said ultrasound wave irradiation transducer also works as said signal receiving transducer.

9. The ultrasound detecting device according to claim 1, wherein
said ultrasound detecting device detects a bone as a target.

10. The ultrasound detecting device according to claim 1, wherein
said ultrasound detecting device detects a tumor/or a degenerated tissue within the body as the target.

11. The ultrasound detecting device according to claim 1, wherein
said ultrasound detecting device is integrated with an ultrasound treatment instrument.

12. The ultrasound detecting device according to claim 1, wherein
a cured state of the target is determined on the basis of temporal change of said stored signal, said analysis result or the determination result by said determination program at the same irradiation position.

* * * * *